United States Patent
Li (10) Patent No.: US 10,582,884 B2
(45) Date of Patent: Mar. 10, 2020

(54) METHOD AND SYSTEM FOR MOTION DATA PROCESSING

(71) Applicant: Shenzhen Microteam Information Technology Co., Ltd, Shenzhen, Guangdong (CN)

(72) Inventor: Youchun Li, Guangdong (CN)

(73) Assignee: Shenzhen Microteam Information Technology Co., Ltd, Shenzhen (CN)

( * ) Notice: Subject to any disclaimer, the term of this patent is extended or adjusted under 35 U.S.C. 154(b) by 0 days.

(21) Appl. No.: 16/251,044

(22) Filed: Jan. 17, 2019

(65) Prior Publication Data

US 2019/0151742 A1 May 23, 2019

Related U.S. Application Data

(63) Continuation of application No. PCT/CN2017/091494, filed on Jul. 3, 2017.

(30) Foreign Application Priority Data

Jul. 18, 2016 (CN) .......................... 2016 1 0571593
Jul. 19, 2016 (CN) ..................... 2016 2 0765977 U
Nov. 18, 2016 (CN) ..................... 2016 2 1255793 U (51) Int. Cl.
*A63B 5/11* (2006.01)
*A61B 5/11* (2006.01)
(Continued)

(52) U.S. Cl.
CPC .......... *A61B 5/1123* (2013.01); *A61B 5/0002* (2013.01); *A61B 5/11* (2013.01); *A61B 5/1122* (2013.01); *A61B 5/6807* (2013.01); *A61B 5/6895* (2013.01); *A63B 43/00* (2013.01); *A63B 69/00* (2013.01); *A63B 69/002* (2013.01); *A63B 71/06* (2013.01); *A63B 71/0622* (2013.01); *A63B 2102/24* (2015.10); *A63B 2220/17* (2013.01); *A63B 2220/18* (2013.01); *A63B 2220/62* (2013.01); *A63B 2220/833* (2013.01); *A63B 2220/836* (2013.01); *A63B 2225/50* (2013.01); *A63B 2230/62* (2013.01); *A63B 2243/0033* (2013.01); *A63B 2243/0037* (2013.01);
(Continued)

(58) Field of Classification Search
None
See application file for complete search history.

(56) References Cited

U.S. PATENT DOCUMENTS

2009/0137933 A1* 5/2009 Lieberman ........... A61B 5/1036 600/595
2009/0210078 A1* 8/2009 Crowley ................ G06Q 30/02 700/91
(Continued)

FOREIGN PATENT DOCUMENTS

CN 102341149 A 2/2012
CN 103372299 A 10/2013
(Continued)

*Primary Examiner* — Jason T Yen (57) ABSTRACT

A method for motion data processing includes: sensing a plurality of motion data of football player by a magnetic football and magnetic sensors; according to the motion data, analyzing the player's motion trajectory by a processing chip, and identifying whether the player's kicking motion is sliding tackle, smashing or dribbling.

6 Claims, 9 Drawing Sheets

(51) Int. Cl.
*A63B 43/00* (2006.01)
*A63B 69/00* (2006.01)
*A63B 71/06* (2006.01)
*A61B 5/00* (2006.01)
*A63B 102/24* (2015.01)

(52) U.S. Cl.
CPC ............... *A63B 2243/0066* (2013.01); *A63B 2243/0095* (2013.01)

(56) References Cited

U.S. PATENT DOCUMENTS

| | | | | |
|---|---|---|---|---|
| 2010/0184563 A1* | 7/2010 | Molyneux | ............ | A43B 1/0054 482/1 |
| 2011/0208444 A1* | 8/2011 | Solinsky | ................ | A61B 5/112 702/41 |

FOREIGN PATENT DOCUMENTS

| | | |
|---|---|---|
| CN | 103861251 A | 6/2014 |
| CN | 104722058 A | 6/2015 |
| CN | 204695344 U | 10/2015 |
| WO | 2015/083990 A | 6/2015 |

* cited by examiner

METHOD AND SYSTEM FOR MOTION DATA PROCESSING

CROSS-REFERENCE TO RELATED APPLICATIONS

The present application is a Continuation Application of PCT Application No. PCT/CN2017/091494 filed on Jul. 3, 2017, which claims the benefit of the Chinese Patent Application No. 201610571593.6, filed with the Chinese Patent Office on Jul. 18, 2016 and entitled "FOOTBALL ACTIVITY DATA COLLECTION METHOD AND SYSTEM", the Chinese Patent Application No. 201620765977.7, filed with the Chinese Patent Office on Jul. 19, 2016 and entitled "BALL", and Chinese Patent Application No. 201621255793.2, filed with the Chinese Patent Office on Nov. 18, 2016 and entitled "SENSING DEVICE AND SPORTS SHOES", which are incorporated herein by reference.

TECHNICAL FIELD

The present application relates to a method and system for motion data processing.

BACKGROUND

Football, known as the "world's first sport", is the most influential individual sport in the global sports world. A standard football match is played by two teams each consisting of 10 players and 1 goalkeeper, a total of 11 players, fighting and attacking on a rectangular grass court. The purpose of the game is to shoot the football into the opponent's goal as much as possible. You can get one point each time you score a goal. When the game is over, the team with the most scores wins. If the scores are the same within the specified time of the game, it depends on a game chapter. The winner can be determined in the form of drawing lots, overtime or reciprocal penalty (12 steps), etc. In a football match, except that the goalkeeper can utilize his hands to touch the football in the penalty area in his own side, each player on the court can only use other parts of the body other than the hands to control the football. Other ball sports, such as basketball and rugby, are sports that humans love very much, with a large number of fans and players.

SUMMARY

An embodiment of present disclosure provides a method for motion data processing. The method includes: sensing a magnetic football provided with a plurality of magnetic sheets or magnetic strips by one of a plurality of magnetic sensors disposed on each football shoe worn by a football player and converting to electrical signal, during training and match; according to the electrical signal, analyzing a ball touch part of the player, a ball touch times and a time point corresponding to the ball touch by a processing chip disposed on each football shoes and connected to the magnetic sensors respectively; according to the ball touch part of the player, the ball touch times and the time point corresponding to the ball touch, generating a first statistical data; according to the ball touch part of the player, the ball touch times, the time point corresponding to the ball touch, a body moving direction and a body inclination angle of the player, generating a second statistical data; according to the first statistical data, identifying the player's ball touch motion for dribbling and passing the football; performing fusion analysis on the body moving direction and the body inclination angle of the player which is collected on a plurality of seconds before and after the time point corresponding to the ball touch to describe a trajectory of the player's kicking motion; with reference to a postural mathematical model established in the cloud, identifying whether the player's kicking motion is sliding tackle, smashing or dribbling.

Another embodiment of the present disclosure provides a system for motion data processing. The system includes: a magnetic football provided with a plurality of magnetic sheets or magnetic strips; a sensing device comprised a processing chip and a plurality of magnetic sensors respectively connected to the processing chip and distributed on upper of the football shoes; wherein the plurality of magnetic sensors configures to sense the magnetic ball and convert a magnetic force into electrical signal to be transmitted to the processing chip and the processing chip configures to perform statistics and analysis according to the electrical signal to obtain ball touch parts of the player, ball touch times and time points corresponding to the ball touch; a six-axis sensor comprised an acceleration sensor configured to sense a body moving direction of the player and record corresponding time point, and a gyro sensor configured to sense a body inclination angle of the player and record corresponding time point; a first communication module disposed on the player and configured to transmit the body moving direction and the body inclination angle of the player to the processing chip in wireless transmission mode; wherein the processing chip further configures to according to the ball touch part of the player, the ball touch times and the time point corresponding to the ball touch, generate a first statistical data; according to the ball touch part of the player, the ball touch times, the time point corresponding to the ball touch, a body moving direction and a body inclination angle of the player, generate a second statistical data; according to the first statistical data, identify the player's ball touch motion for dribbling and passing the football; perform fusion analysis on the body moving direction and the body inclination angle of the player which is collected on a plurality of seconds before and after the time point corresponding to the ball touch to describe a trajectory of the player's kicking motion; with reference to a postural mathematical model established in the cloud, identify whether the player's kicking motion is sliding tackle, smashing or dribbling.

BRIEF DESCRIPTION OF DRAWINGS

One or more embodiments are illustratively described by the drawings in the corresponding accompanying drawings. The illustrative descriptions are not intended to limit the embodiments, and the drawings in the accompanying drawings do not constitute a scale limitation unless specifically stated otherwise.

DETAILED DESCRIPTION

To make the objectives, technical solutions, and advantages of the present application clearer and more comprehensible, the following further describes the present application in detail with reference to the accompanying drawings and embodiments. It should be understood that the specific embodiments described herein are merely used to explain the present application and are not intended to limit the present application.

Ball sports refer in the application include football, handball, basketball, volleyball, rugby, hockey, etc. Taking football as an example, the present application is described in detail below with reference to the accompanying drawings and embodiments.

Embodiment 1

Figure 1:
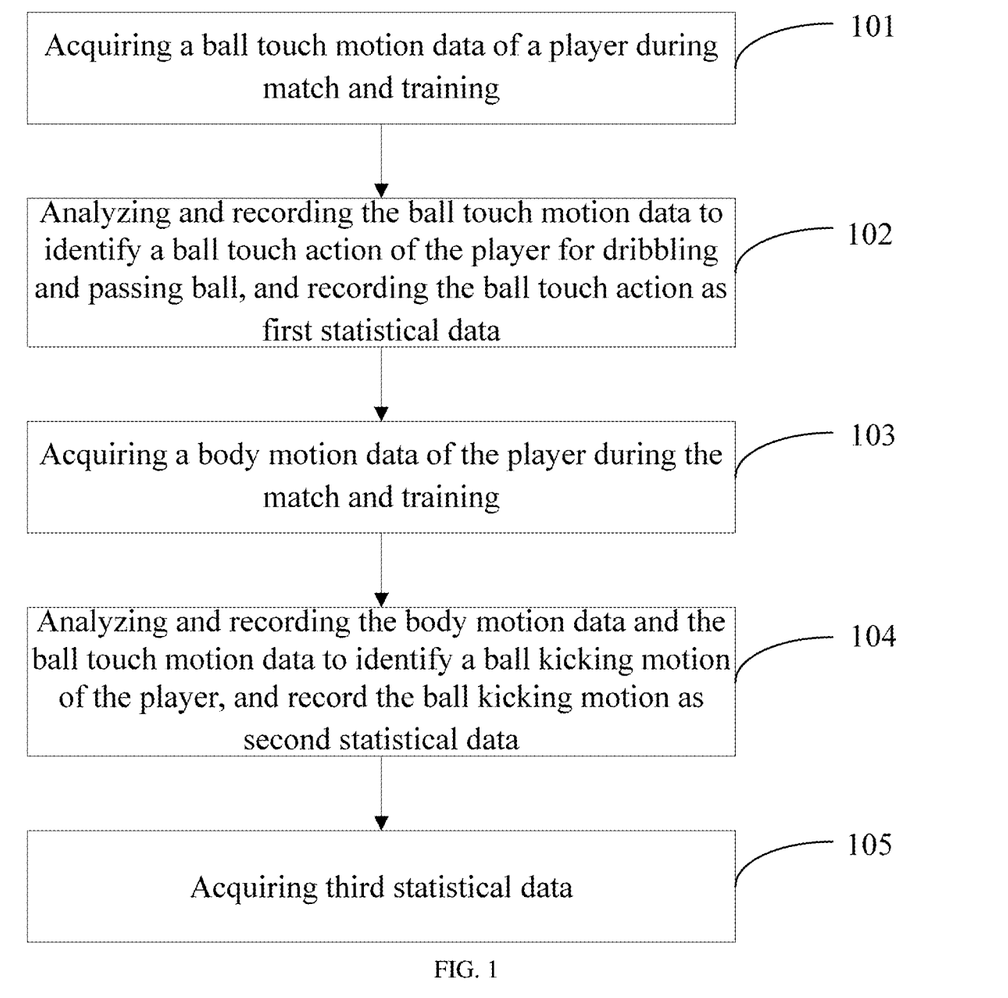
FIG. 1 is a flowchart of a method for motion data processing according to embodiment 1 of the present application.

Referring to FIG. 1, a method for motion data processing includes:

Step 101: Acquiring a ball touch motion data of a player during match and training.

During training and match, a used ball is provided therein with magnetic sheets or magnetic strips to make the football magnetic;

a sensing device is disposed on each football shoe worn by a football player, and the sensing device includes a plurality of magnetic sensors and a processing chip; the plurality of magnetic sensors is respectively connected to the processing chip, and the plurality of magnetic sensors are distributed at a plurality of parts of an upper of the football shoe. The magnetic sensor may sense a football within 1 cm away from the magnetic sensor and convert a magnetic force into a first electrical signal to be transmitted to the processing chip.

The processing chip performs statistics and analysis according to the received first electrical signal to obtain the player's ball touch motion data, and the ball touch motion data includes ball touch parts of the left and right feet of the player, ball touch times, and time points corresponding to the ball touch.

Step 102: Analyzing and recording the ball touch motion data to identify a ball touch action of the player for dribbling and passing ball, and recording the ball touch action as first statistical data.

The processing chip identifies the ball touch motion of the player for dribbling and passing the ball, i.e., first statistical data, according to counted specific ball touch parts of the feet and the ball during the player's kicking the ball, ball touch times, and time points corresponding to the ball touch.

Step 103: Acquiring a body motion data of the player during the match and training.

The player's body motion data includes body moving directions and body inclination angles of the player.

During training and match, the player carries a six-axis sensor on his body. The six-axis sensor includes an acceleration sensor and a gyro sensor. When the player's body moves forward, backward, leftwards, or rightwards, the acceleration sensor can sense a direction in which the player's body moves. When the player's body is inclined forward, backward, leftwards, or rightwards, the gyro sensor can sense a direction and an angle of the body inclination of the player, and record a time point corresponding to each body moving direction and a time point corresponding to each body inclination angle.

Step 104: Analyzing and recording the body motion data and the ball touch motion data to identify a ball kicking motion of the player, and record the ball kicking motion as second statistical data.

The processing chip identifies the player's ball kicking motion of dribbling and passing the ball, i.e., second statistical data, according to counted specific ball touch parts of the feet and the ball during the player's kicking the ball, ball touch times, and time points corresponding to the ball touch.

Step 105: Acquiring third statistical data.

The processing chip transmits the first statistical data or the second statistical data acquired after the analysis to a central processing unit outside the court by wirelessly connecting which is established by a fourth communication module disposed outside the court to a second communication module disposed on a football shoe.

The central processing unit performs further statistics and analysis on the received first statistical data and second statistical data of each player on the court.

During the match or training, the central processing unit provides the ball control rates, pass times and ball control time of both teams, i.e., the third statistical data, according to results of statistics and analysis in real time.

Coaching staff can analyze technical problems of individual football players of the team and technical and tactical problems of the team as a whole according to the football players' ball kicking motion as well as ball control rates, pass times and ball control time of both teams, and guide each football player and the team's football players to conduct more scientific and reasonable training.

Embodiment 2

Figure 2:
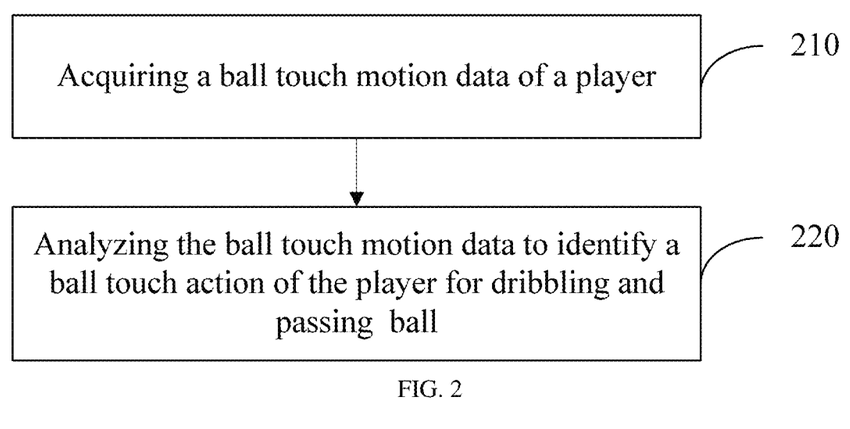
FIG. 2 is a flowchart of a method for motion data processing according to embodiment 2 of the present application.

Referring to FIG. 2, a method for motion data processing includes:

Step 210: Acquiring a ball touch motion data of a player.

Magnetic sheets or magnetic strips are disposed inside a ball used during training or match to make the ball magnetic; a sensing device is disposed on each football shoe worn by a football player, and the sensing device includes a plurality of magnetic sensors and a processing chip; the plurality of magnetic sensors are respectively connected to the processing chip, and the plurality of magnetic sensors is distributed at a plurality of parts of an upper of the football shoe. The magnetic sensor may sense a football within 1 cm away from the magnetic sensor and convert a magnetic force into a first electrical signal to be transmitted to the processing chip.

The processing chip performs statistics and analysis according to the received first electrical signal to obtain the player's ball touch motion data, and the ball touch motion data includes ball touch parts of the left and right feet of the player, ball touch times, and time points corresponding to the ball touch.

Step 220: Analyzing the ball touch motion data to identify a ball touch action of the player for dribbling and passing ball.

Different from traditional situation, in this embodiment, the player's ball touch motion data and body motion data are acquired, and the ball touch action of each player and the ball control rates, pass times, and ball control time of both teams in ball sports are analyzed by statistical analysis on the ball touch motion data and body motion data.

Embodiment 3

Figure 3:
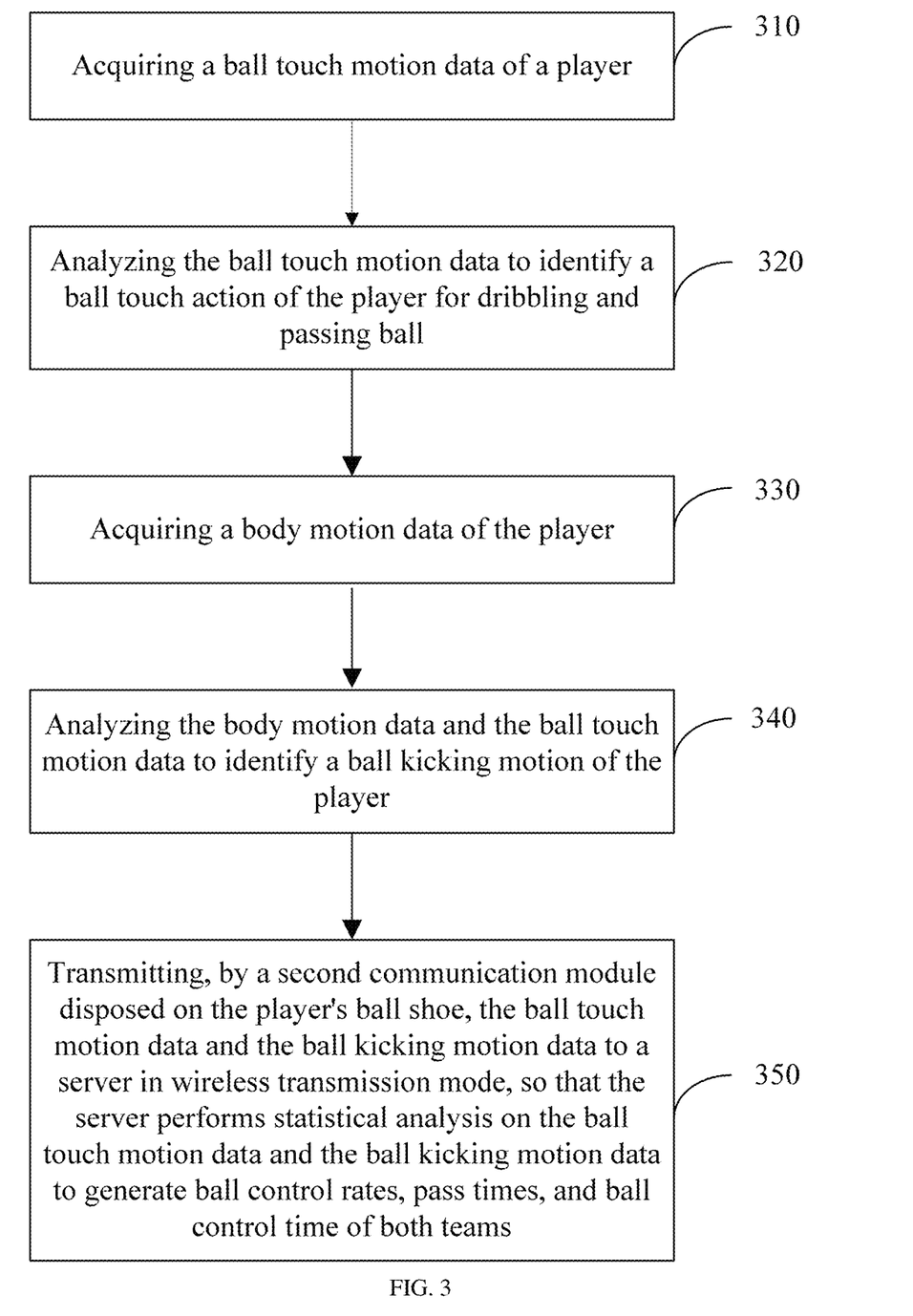
FIG. 3 is a flowchart of a method for motion data processing according to embodiment 3 of the present application.

Referring to FIG. 3, a method for motion data processing includes:

Step 310: Acquiring a ball touch motion data of a player.

Figure 4:
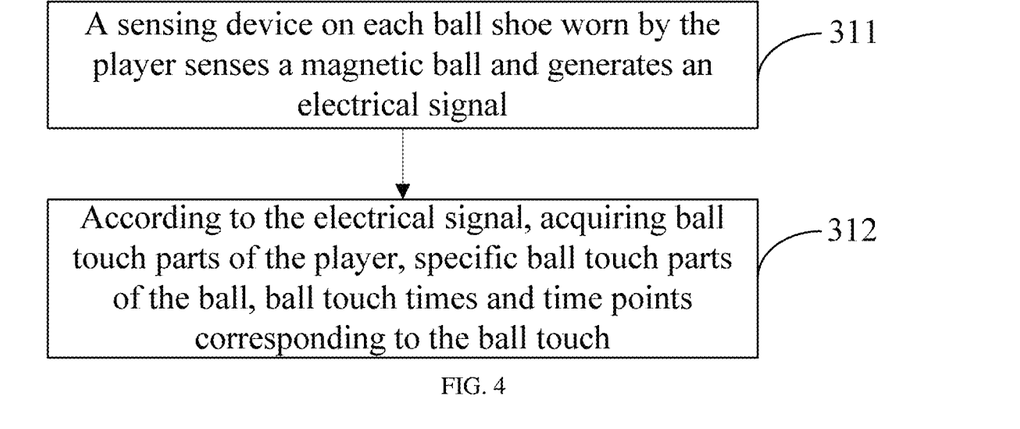
FIG. 4 is a flowchart of acquiring body motion data of the player according to embodiment 3 of the present application.

Referring to FIG. 4, the specific step of acquiring a player's ball touch motion data includes:

Step 311: A sensing device on each ball shoe worn by the player senses a magnetic ball and generates an electrical signal.

Step 312: According to the electrical signal, acquiring ball touch parts of the player, specific ball touch parts of the ball, ball touch times and time points corresponding to the ball touch.

The ball touch motion data includes ball touch parts of the player, ball touch times, and time points corresponding to the ball touch. Magnetic sheets or magnetic strips are disposed inside a ball used during training or match to make the ball magnetic; a sensing device is disposed on each football shoe worn by a football player, and the sensing device includes a plurality of magnetic sensors and a processing chip; the plurality of magnetic sensors is respectively connected to the processing chip, and the plurality of magnetic sensors are distributed at a plurality of parts of an upper of the football shoe. The magnetic sensor may sense a football within 1 cm away from the magnetic sensor and convert a magnetic force into a first electrical signal to be transmitted to the processing chip.

Step 320: Analyzing the ball touch motion data to identify a ball touch action of the player for dribbling and passing ball.

Step 330: Acquiring a body motion data of the player.

The body motion data includes body moving directions and body inclination angles of the player; and during training and match, the player carries a six-axis sensor on his body. The six-axis sensor includes an acceleration sensor and a gyro sensor. When the player's body moves forward, backward, leftwards or rightwards, the acceleration sensor can sense a direction in which the player's body moves. When the body is inclined forward, backward, leftwards, or rightwards, the gyro sensor can sense the direction and angle of the body inclination direction and angle, and record a time point corresponding to each body moving direction and a time point corresponding to each body inclination angle.

Figure 5:
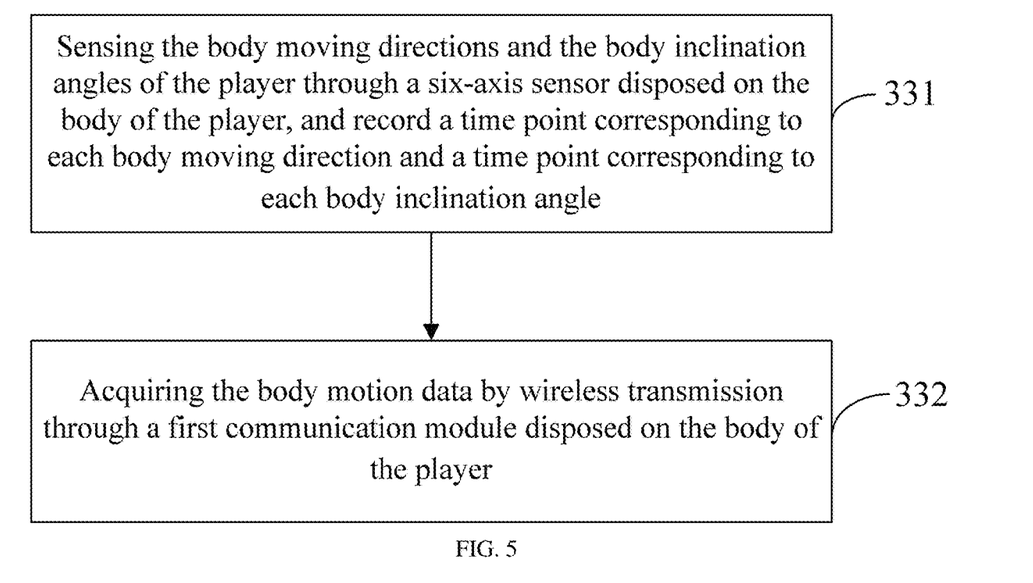
FIG. 5 is a flowchart of acquiring ball touch motion data of the player according to embodiment 3 of the present application

Referring to FIG. 5, the specific step of acquiring a body motion data of the player includes: Step 331: Sensing the body moving directions and the body inclination angles of the player through a six-axis sensor disposed on the body of the player, and record a time point corresponding to each body moving direction and a time point corresponding to each body inclination angle. Step 332: Acquiring the body motion data by wireless transmission through a first communication module disposed on the body of the player.

Step 340: Analyzing the body motion data and the ball touch motion data to identify a ball kicking motion of the player.

The processing chip identifies the player's ball kicking motion of dribbling and passing a ball, according to counted specific ball touch parts of the feet and the ball during the player's kicking the ball, ball touch times, and time points corresponding to the ball touch.

Step 350: Transmitting, by a second communication module disposed on the player's ball shoe, the ball touch motion data and the ball kicking motion data to a server in wireless transmission mode, so that the server performs statistical analysis on the ball touch motion data and the ball kicking motion data to generate ball control rates, pass times, and ball control time of both teams.

During match or training, the central processing unit provides the ball control rates, pass times and ball control time of both teams according to results of statistics and analysis in real time.

To implement the method for motion data processing described in Embodiments 1-3, an embodiment of the present application further provides a device for motion data processing. The apparatus for ball sports data collection includes a sensing unit, an identification unit, and a transmitting unit. The sensing unit is configured to acquire a player's ball touch motion data. Specifically, the sensing unit is specifically configured to sense a magnetic ball through a sensing device on each ball shoe worn by the player, generate an electrical signal, and acquire, according to the electrical signal, ball touch parts of the player, specific ball touch parts of the ball, ball touch times, and time points corresponding to the ball touch. The identification unit is configured to analyze the ball touch motion data to identify the player's ball touch motion of dribbling and passing a ball. The sensing unit is also configured to acquire the player's body motion data; specifically, the sensing unit is configured to sense the body moving directions and the body inclination angles of the player through a six-axis sensor disposed on the body of the player, and record a time point corresponding to each body moving direction and a time point corresponding to each body inclination angle; and acquire the body motion data through a first communication module disposed on the body of the player in a wireless transmission mode. The identification unit is configured to analyze the body motion data and the ball touch motion data to identify the player's ball kicking motion. The transmitting unit is configured to transmit, by a second communication module disposed on the player's ball shoe, the ball touch motion data and the ball kicking motion data to a server in a wireless transmission mode, so that the server performs statistical analysis on the ball touch motion data and the ball kicking motion data to generate ball control rates, pass times, and ball control time of both teams.

Figure 6:
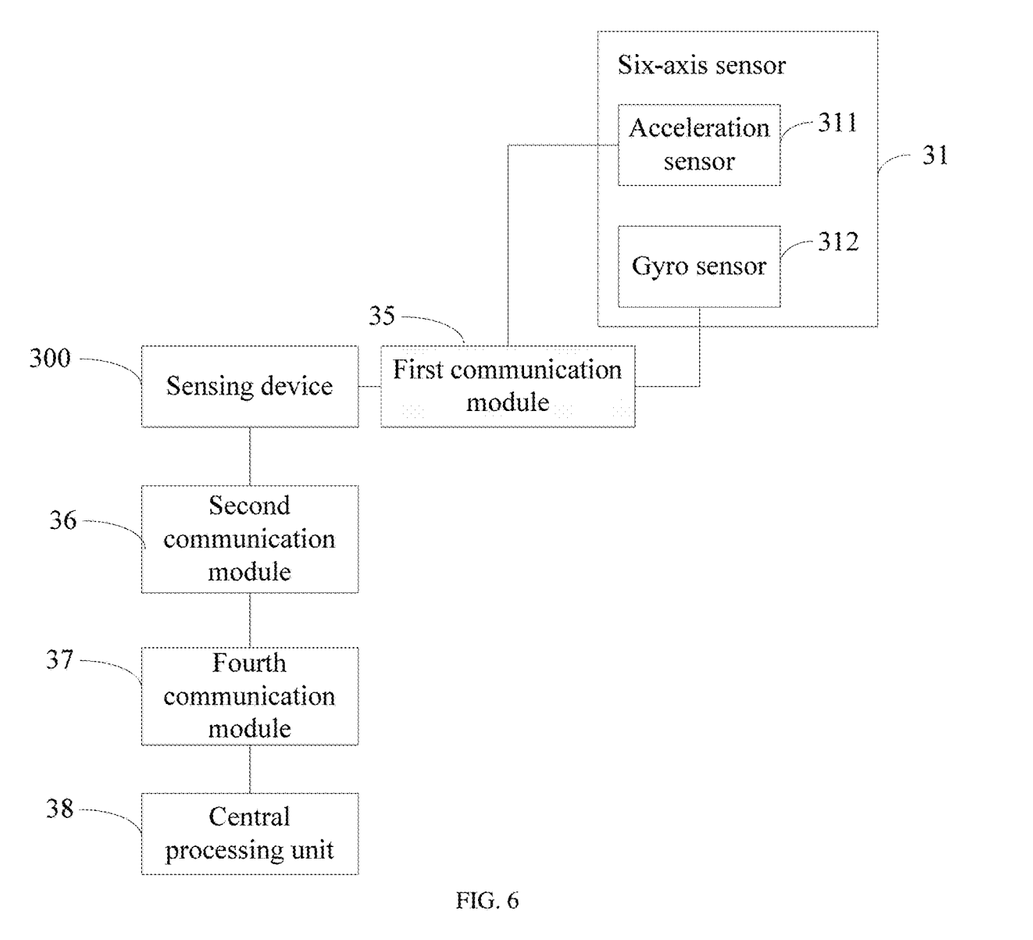
FIG. 6 is a schematic structural diagram of a system for motion data processing according to an embodiment of the present application.
Figure 7:
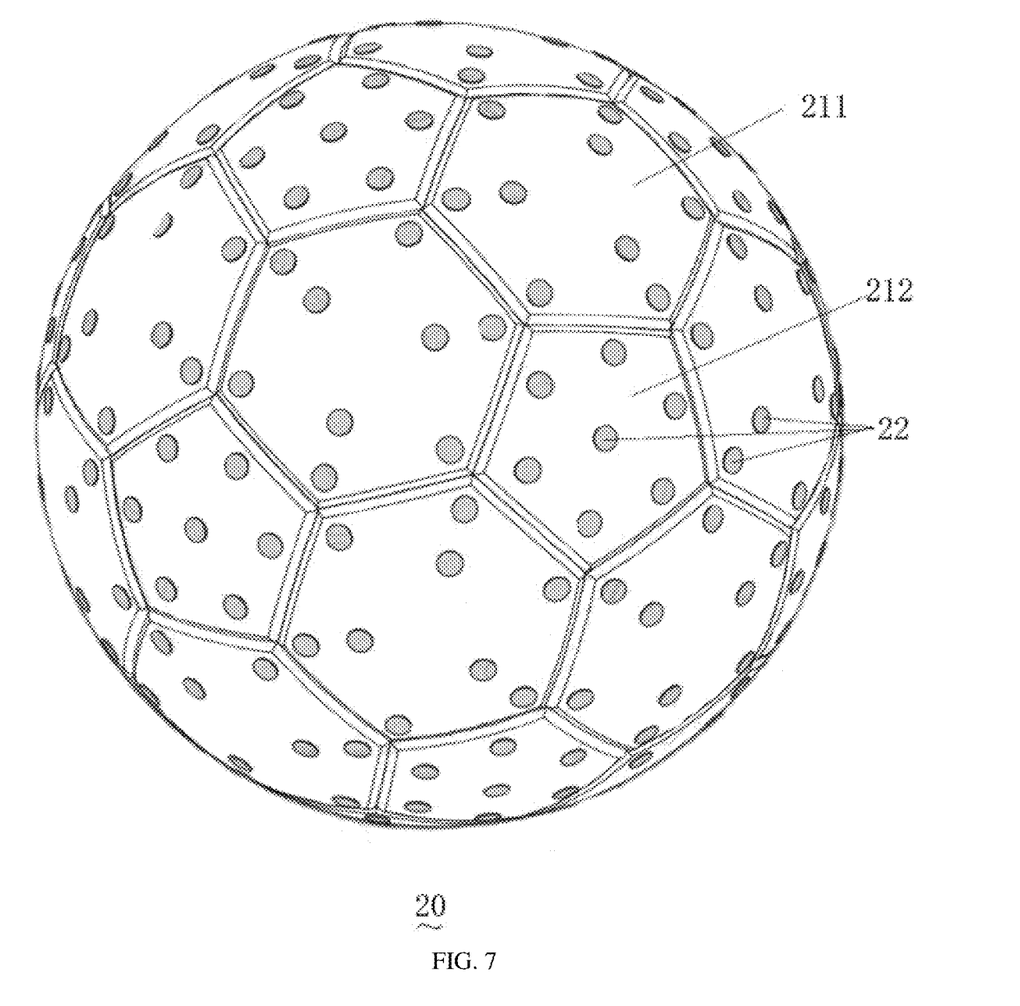
FIG. 7 is a solid diagram of ball in the system for motion data processing according to an embodiment of the present application.

Referring to FIGS. 6 and 7, to implement the method for motion data processing described in Embodiments 1-3, an embodiment of the present application further provides a system for motion data processing, including a ball 20, a six-axis sensor 31, a first communication module 35, a second communication module 36, a central processing unit 38, and a sensing device 300.

The system for motion data processing is described in detail below by taking football sports as an example. FIG. 7 is a solid diagram of a ball in an embodiment of the present application. As shown in FIG. 7, the ball 20 includes an inner bladder (not shown), a casing 21, and a plurality of magnetic sheets 22. The casing 21 wraps the inner bladder; the magnetic sheets 22 are located between the casing 21 and the inner bladder, and the magnetic sheets 22 are fixed on an inner surface of the casing 21.

The casing (not shown) includes a plurality of polygonal casing sheets (not shown), and the casing 21 is formed by splicing a plurality of polygonal casing sheets; and the magnetic sheets 22 are fixed on the polygonal casing sheets. The polygonal casing sheets include regular hexagonal casing sheets 211 and regular pentagonal casing sheets 212, and the hexagonal casing sheets 211 and the pentagonal casing sheets 212 are connected to each other.

The polygonal casing sheets include regular pentagonal casing sheets 212; each regular pentagonal casing sheet 212 has seven magnetic sheets 22; the seven magnetic sheets 22 are evenly distributed on an inner surface of the regular pentagonal casing sheet 212, and a distance between two adjacent magnet sheets 22 is the same. Such a design enables the regular hexagonal casing sheets 212 to have a sufficient number of magnetic sheets 22, which can ensure that when any part is touched during the use of the ball 20, the magnetic sheets 22 located on this part can be sensed by an external magnetic sensor at the first time.

The polygonal casing sheets include regular hexagonal casing sheets 211; each regular hexagonal casing sheet 211 has nine magnetic sheets 22; three magnetic sheets 22 are located at a middle portion of the regular hexagonal casing sheet 211, and six magnetic sheets 22 are distributed at an edge of the regular hexagonal casing sheet 211. Such a design enables the regular hexagonal casing sheets 211 to have a sufficient number of magnetic sheets 22, which can ensure that when any part is touched during the use of the ball 20, the magnetic sheets 22 located on this part can be sensed by an external magnetic sensor at the first time.

A length and a width of each magnetic sheet 22 are no more than 3 mm, and a thickness thereof is 0.5-1.5 mm. The magnetic sheet 22 may be a circular sheet or is in a rectangular shape, a long strip shape, and the like, as long as each part of the ball 20 is magnetic. It can be seen that the volume of the magnetic sheet 22 is small, and the circumference of the ball is about 69 cm, which is in the range of 68.5-69.5 cm. The volume of the ball 20 is not increased by the presence of the magnetic sheet 22, so that the player's normal ball kicking is not affected. The size of the ball can be varied to suit different usage requirements. In this embodiment, the ball 20 is a football, and the ball 20 is a No. 5 ball. The ball 20 provided in the embodiment of the present application may also be applied to footballs of other models, such as a No. 3 ball and a No. 4 ball (the No. 3 ball is a ball for children to learn and train; the No. 4 ball is a ball special for a 5-player or 7-player field, and the No. 5 ball is a ball for regular games).

Each magnetic sheet 22 is formed by bonding micro-sized NdFeB magnet steel with a bonding thickness of about 1 mm by latex heating (no more than 80° C.). The magnetic sheet 22 is circular, and has a diameter of 3 mm. Moreover, the weight of each magnetic sheet 22 is 0.1 g, and thus the weight of the ball 20 is not increased too much. The overall weight of the ball 20 is controlled at about 420 g, which fully meets the requirements of FIFA (410-450 g). It should be specially stated that to make the ball magnetic, it is also possible to add a magnetic rubber inside the ball (the magnetic rubber is one of a series of ferrite magnets, which is formed by compounding bonded ferrite magnetic powder and synthetic rubber, and is a flexible, elastic and twistable magnet formed by extrusion molding, calendaring molding, injection molding, or the like. The magnetic rubber can be processed into a strip shape, a roll shape, a sheet shape, a block shape, a ring shape, and various complex shapes.) Specifically, magnetic powder is added to a ball production material, and is evenly distributed on the surface of the ball.

The inner bladder and the casing (not shown) of the ball 20 are made of a highly elastic material, and the feeling for kicking the ball 20 is superior when players play the ball.

The application effect of the ball 20 of the embodiment of the present application is: a plurality of magnetic sheets 22 is evenly disposed between the inner bladder and the casing 21 of the ball 20, and these magnetic sheets 22 have a small volume and each have a weight of about 0.1 g, so that the overall weight of the ball 20 is controlled at around 420 g, which fully meets the requirements of FIFA (410-450 g). Therefore, the football player will not feel the ball 20 becomes larger or heavier during use, even the presence of the magnetic sheets 22. Thereby, the affecting of the football player's feeling is avoided.

The magnetic sensors in an external sensing system can detect changes of a minimum 2-5 Gaussian magnetic field strength at a distance of about 1 cm from the ball, so that the magnetic sensors can sense a magnetic field of magnetic sheets 22 located on an inner surface of the casing (not shown) when the distance from the ball 20 is about 1 cm, thereby detecting whether the football player touches the ball according to the changes in the magnetic field. When there is an out-of-bounds ball in a football match, it is often difficult for a referee to determine which player is the last person to touch the ball, and even misjudgment may occur, affecting the fairness of the match. However, when the ball 20 is used in the match, the magnetic sheets 22 on the ball 20 can detect which player has touched the ball finally and can help the referee to make decisions.

The six-axis sensor 31 includes an acceleration sensor 311 and a gyro sensor 312, and both the acceleration sensor 311 and the gyro sensor 312 are fixed to the body of the player. When the player's body moves forward, backward, leftwards, or rightwards, the acceleration sensor 311 can sense a direction in which the player's body moves. When the player's body is inclined forward, backward, leftwards, or rightwards, the gyro sensor 312 can sense a direction and an angle of the body inclination of the player, and record a time point corresponding to each body moving direction and a time point corresponding to each body inclination angle.

The first communication module 35 is fixed on the player's body and electrically connected to the six-axis sensor 31; the second communication module 36 is fixed on a football shoe and electrically connected to the sensing device 300; and a fourth communication module 37 is located outside a court and directly electrically connected to the central processing unit 38.

In the embodiment provided by the present application, the sensing device 300 of the system for motion data processing can be used as a separate product. As its used, the sensing device 300 needs to be fixed on an outer surface of a common football shoe and configured to sense the ball 20 to acquire the player's ball touch motion data, analyze the ball touch motion data, and identify the player's ball touch motion of dribbling and passing the ball. It can be understood that the sensing device 300 may also be disposed inside the football shoe as part of the football shoe, thereby making the football shoe with the sensing device 300 be a smart ball shoe having a data collecting function. The above two cases will be separately described below in two embodiments.

Embodiment 4

Figure 8:
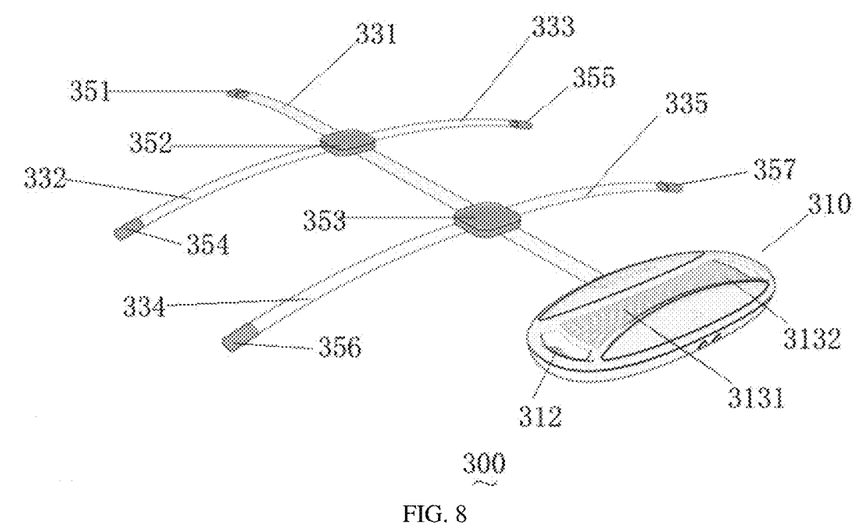
FIG. 8 is a schematic structural diagram of a sensing device according to Embodiment 4 of the present application.

Referring to FIG. 8, the sensing device 300 includes a housing 310, a processing chip 33, a first bobbin 331, a first connecting line (not shown), and a first magnetic sensor 351, where the housing 310 is provided with a receiving space and fixing holes 312; the processing chip 33 is fixed in the receiving space; one end of the first bobbin 331 is fixed to the housing 310, and one end of the first bobbin 331 communicates with the receiving space 211; the first connecting line is embedded in the first bobbin 331, and one end of the first connecting line is connected to the processing chip 33; and the first magnetic sensor 351 is connected to the other end of the first connecting line. The first magnetic sensor 351 can convert the sensed external magnetic force into a first electrical signal, and transmit the electrical signal to the processing chip through the first connecting line, and the processing chip 33 can analyze and record the received electrical signal.

There are four fixing holes 312, respectively a first fixing hole (not shown), a second fixing hole (not shown), a third fixing hole (not shown), and a fourth fixing hole (not shown). The first fixing hole and the second fixing hole are located at one side of the housing 310, and the third fixing hole and the fourth fixing hole are located at the other side of the housing 310.

The housing 310 is further provided with a first fixing groove 3131 and a second fixing groove 3132. The first fixing groove 3131 and the second fixing groove 3132 are staggered. Two ends of the first fixing groove 3131 communicate with the first fixing hole and the fourth fixing hole respectively; and the two ends of the second fixing groove 3132 communicate with the second fixing hole and the third fixing hole, respectively. A shoe lace passes through the fixing hole 312 and is embedded in the first fixing groove 3131 and the second fixing groove 3132 to fix the housing 310 to a tongue.

The sensing device 300 further includes a second magnetic sensor 352 and a second connecting line (not shown). The second magnetic sensor 352 is fixed on the first bobbin 331, and the second magnetic sensor 352 is located between the first magnetic sensor 351 and the processing chip 33. The second connecting line is embedded in the first bobbin 331. One end of the second connecting line is connected to the processing chip 33, and the other end is connected to the second magnetic sensor 352. The second magnetic sensor 352 can convert the sensed external magnetic force into a second electrical signal, and transmit the electrical signal to the processing chip 33 through the second connecting line, and the processing chip 33 can analyze and record the received electrical signal.

The sensing device 300 further includes a third magnetic sensor 353 and a third connecting line (not shown), the third magnetic sensor 353 is fixed on the first bobbin 331, and the third magnetic sensor 353 is located between the second magnetic sensor 352 and the processing chip 33. The third connecting line is embedded in the first bobbin 331. One end of the third connecting line is connected to the processing chip 33, and the other end is connected to the third magnetic sensor 353. The third magnetic sensor 353 can convert the sensed external magnetic force into a third electrical signal, and transmit the electrical signal to the processing chip 33 through the third connecting line, and the processing chip 33 can analyze and record the received electrical signal.

The sensing device 300 also includes a fourth magnetic sensor 354, a second bobbin 332, and a fourth connecting line (not shown); the fourth magnetic sensor is fixed at one end of the second bobbin 332, and the other end of the second bobbin 332 is fixed to and communicates with the first bobbin 331; one end of the fourth connecting line is connected to the fourth magnetic sensor 354, and the other end of the fourth connecting line sequentially passes through the second bobbin 332 and part of the first bobbin 331 and then is connected to the processing chip 33. The fourth magnetic sensor 354 can convert the sensed external magnetic force into a fourth electrical signal, and transmit the electrical signal to the processing chip 33 through the fourth connecting line, and the processing chip 33 can analyze and record the received electrical signal.

The sensing device 300 also includes a fifth magnetic sensor 355, a third bobbin 333, and a fifth connecting line (not shown); the fifth magnetic sensor 355 is fixed at one end of the third bobbin 333, and the other end of the third bobbin 333 is fixed to and communicates with the first bobbin 331; one end of the fifth connecting line is connected to the fifth magnetic sensor 355, and the other end of the fifth connecting line sequentially passes through the third bobbin 333 and part of the first bobbin 331 and then is connected to the processing chip 33. The fifth magnetic sensor 355 can convert the sensed external magnetic force into a fifth electrical signal, and transmit the electrical signal to the processing chip 33 through the fifth connecting line, and the processing chip 33 can analyze and record the received electrical signal.

The third bobbin 333 and the second bobbin 332 are located at two sides of the first bobbin 331 respectively, and a connection point between the third bobbin 333 and the first bobbin 331 is the same as a connection point between the second bobbin 332 and the first bobbin 331. The third magnetic sensor 353 is located at a connection point between the third bobbin 333 and the first bobbin 331.

The sensing device 300 also includes a sixth magnetic sensor 356, a fourth bobbin 334, and a sixth connecting line (not shown); the sixth magnetic sensor 356 is fixed at one end of the fourth bobbin 334, and the other end of the fourth bobbin 334 is fixed to and communicates with the first bobbin 31; one end of the sixth connecting line is connected to the sixth magnetic sensor 356, and the other end of the sixth connecting line sequentially passes through the fourth bobbin 34 and part of the first bobbin 331 and then is connected to the processing chip 33. The sixth magnetic sensor 356 can convert the sensed external magnetic force into a sixth electrical signal, and transmit the electrical signal to the processing chip 33 through the sixth connecting line, and the processing chip 33 can analyze and record the received electrical signal.

The sensing device 300 also includes a seventh magnetic sensor 357, a fifth bobbin 335, and a seventh connecting line (not shown); the seventh magnetic sensor 357 is fixed at one end of the fifth bobbin 335, and the other end of the fifth bobbin 335 is fixed to and communicates with the first bobbin 331; one end of the seventh connecting line is connected to the seventh magnetic sensor 357, and the other end of the seventh connecting line sequentially passes through the fifth bobbin 335 and part of the first bobbin 331 and then is connected to the processing chip 33. The seventh magnetic sensor 357 can convert the sensed external magnetic force into a seventh electrical signal, and transmit the electrical signal to the processing chip 33 through the seventh connecting line, and the processing chip 33 can analyze and record the received electrical signal.

It should be noted that when the sensing device 300 needs to detect a specific part of an upper of a football shoe where an external magnetic force is applied more accurately, a same mode as the second bobbin 332 and the fourth connecting line can be adopted, and more connecting lines are fixed on the first connecting line; at the same time, the two ends of the connecting lines and joints of the connecting lines are provided with sensors, which are configured to sense the external magnetic force applied to the upper of the football shoe.

The application of the sensing device 300 of the embodiment of the present application is as follows: when a wearer puts on football shoes equipped with the sensing devices 300 to play football, since a first magnetic sensor 351, a second magnetic sensor 352, a third magnetic sensor 353, a fourth magnetic sensor 354, a fifth magnetic sensor 355, a sixth magnetic sensor 356, and a seventh magnetic sensor 357 are fixed on a plurality of parts of the upper of each football shoe respectively. The football magnetically stimulates the first magnetic sensor 351, the second magnetic sensor 352, the third magnetic sensor 353, the fourth magnetic sensor 354, the fifth magnetic sensor 355, the sixth magnetic sensor 356, and the seventh magnetic sensor 357 on the touch parts of the upper when the wearer touches the football with the foot. The magnetic stimulation to the magnetic sensors is converted into an electrical signal to be transmitted to the processing chip through the connecting line. The processing chip can acquire ball touch parts according to the electrical signal received from the touch parts of the upper, and the ball touch times (left and right feet) of the wearer are calculated according to the receiving times of the electrical signal and recorded. Further, the sensing device 300 helps a football player or football fan to practice arc shot in the daily football training (the arc shot is also called "curve ball", "banana ball", which is a technical term in football sports. The screw arc shot refers to a kicking technique in which the player uses a foot method to kick the ball and make the ball run in the air in an arc. The arc shot is often used when the attacker gets a direct free kick near the opponent's penalty area, using an arc running state to avoid a wall and directly shoot for scoring). The sensing device 300 helps the kicker find the best part of implementing the arc shot with the foot by sensing and recording the ball touch parts when the kicker practices the arc shot. The football player or football fan can quickly and better master this kicking technique with the help of the sensing device 300.

Figure 9:
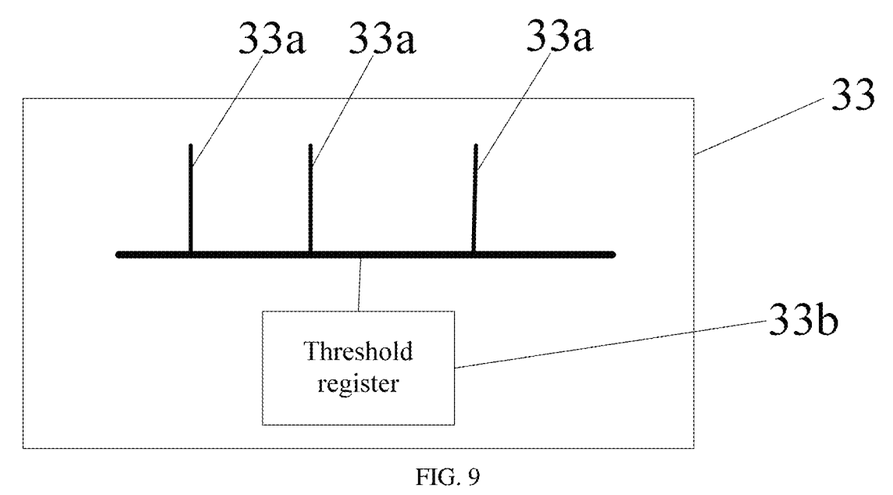
FIG. 9 is a schematic structural diagram of a processing chip in the system for motion data processing according to an embodiment of the present application.

As shown in FIG. 9, the processing chip 33 is provided with three or more address lines 33a in order to support a plurality of magnetic sensors (351, 352, 353, 354, 355, 356, and 357) to make the wiring simpler. A communication mode between the processing chip and the magnetic sensor is IIC, and a problem of how to perform address selection of the processing chip 33 exists in the communication process. Traditional chip is only provided with one address line, and two addresses (a 1-bit address line can only set two addresses by setting this bit to "0" or "1") can only be set for the magnetic sensors (351, 352, 353, 354, 355, 356, and 357) through one address line, which apparently cannot meet the needs of the product. The ball shoe has eight magnetic sensors, which correspond to eight different addresses. Two NC pins and a preceding inherent address line can be used to form a three-position address selection line, and the setting of eight (23) different addresses is achieved by setting the level of the three-position address line, to solve the problem of the plurality of magnetic sensors (351, 352, 353, 354, 355, 356, and 357). The processing chip 33 is further provided with a threshold register 33b. When the magnetic ball 20 approaches, the preset threshold is reached, and a certain pin of the magnetic sensors (351, 352, 353, 354, 355, 356, and 357) is triggered to output high or low levels for the determination by the processing chip 33. By reporting to the processing chip 33 by means of the threshold register, a problem that an traditional processing chip 33 needs to constantly poll all the magnetic sensors (351, 352, 353, 354, 355, 356, and 357) for real-time variation, which brings about large power consumption is solved.

During training and match, a used ball is provided therein with magnetic sheets or magnetic strips to make the ball magnetic. The ball is a football including an inner bladder and a casing. The casing wraps the inner bladder, and a plurality of magnetic sheets is located between the inner bladder and the casing. A sensing device (not shown) is disposed on each football shoe worn by a football player, and the sensing device includes a plurality of magnetic sensors (351, 352, 353, 354, 355, 356, and 357) and a processing chip 33; the plurality of magnetic sensors (351, 352, 353, 354, 355, 356, and 357) are respectively connected to the processing chip 33, and the plurality of magnetic sensors (351, 352, 353, 354, 355, 356, and 357) is distributed on a plurality of parts of an upper of the football shoe. The magnetic sensors (351, 352, 353, 354, 355, 356, and 357) may sense a football within 1 cm away from the magnetic sensors and convert a magnetic force into a first electrical signal for transmission to the processing chip 33.

Embodiment 5

Figure 10:
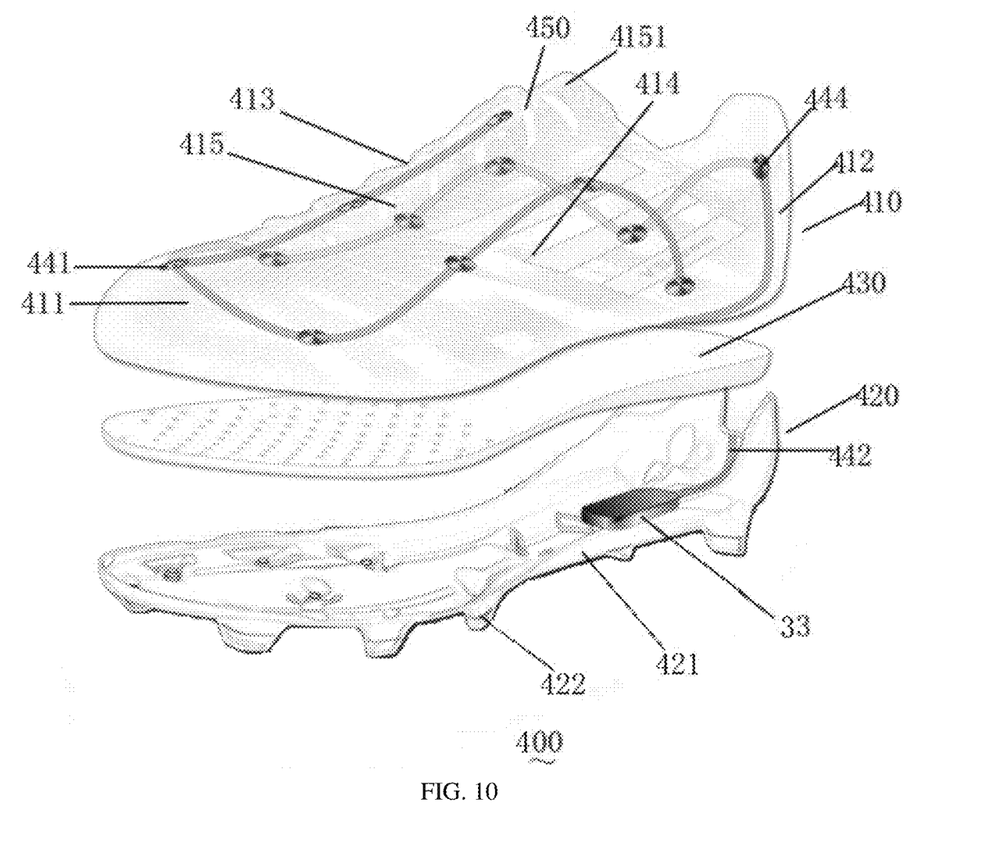
FIG. 10 is a schematic structural diagram of a sensing device according to embodiment 5 of the present application.

As shown in FIG. 10, a sports shoe 400 includes an upper 410, a sole 420, and a sensing device 300. The upper 410 covers an upper surface of the sole 420 and is integrally fixed with the sole; a portion of the sensing device 300 is located inside the upper 410, and the other portion is located inside the sole 420. The sensing device 300 includes a first magnetic sensor 441, and the first magnetic sensor 441 is located in the upper 410.

The upper 410 includes a tiptoe portion 411, a heel portion 412, an inner instep portion 413, an outer instep portion 414, and an instep portion 415, where the instep portion 415 is provided with a tongue 4151 and a plurality of shoe holes 4152; and a shoe lace 450 passes through the shoe holes 4152. When worn, by tightening and knotting the shoe lace 450, the sports shoe 400 is fixed on the foot. The tongue 4151 is located at the instep portion 415 of the upper 410, and the tongue is elastic and can relieve the pressure on the instep.

The sports shoe 400 further includes an insole 430 and a shoe lace 450. The insole 430 is located within a cavity defined by the upper 410 and the sole 420 and abuts against an upper surface of the sole 420. The insole has a buffering effect during the movement of the wearer, to achieve a damping effect.

The sole 420 includes a base body 421 and shoe tacks 422. The base body 421 is in a plate shape and the shoe tacks 422 is a plurality of protrusions extended downwards out of a lower surface of the base body 421. The base body 421 includes a front bottom portion and a heel portion.

The sensing device 300 further includes a second magnetic sensor 444, a third magnetic sensor, a fourth magnetic sensor, a fifth magnetic sensor, a connecting line 442, a processing chip 33, and a battery (not shown), and the main function of the sensing device is to output an electrical signal after being subjected to an external magnetic field. The first magnetic sensor 441 is located at the tiptoe portion 411 of the upper 410, the second magnetic sensor 444, the third magnetic sensor (not shown), the fourth magnetic sensor (not shown), and the fifth magnetic sensor (not shown) are located at the heel portion 412, the inner instep portion 413, the outer instep portion 414, and the instep portion 415 of the upper, respectively. The second magnetic sensor 444, the third magnetic sensor, the fourth magnetic sensor, and the fifth magnetic sensor are connected to the processing chip 33 and the battery.

It should be noted that the first magnetic sensor 441 can also be fixed inside the heel portion 412 of the base body 421 in the sole 420. Preferably, in the embodiment, as shown in FIG. 2, a second magnetic sensor 444 is fixed at the tiptoe portion 411 of the upper 410; a first magnetic sensor 441 is fixed at the heel portion 412; three third magnetic sensors (not shown) are fixed at the inner instep portion 413; three fourth magnetic sensors (not shown) are fixed at the outer instep portion 414; and three fifth magnetic sensors (not shown) are fixed at the instep portion 415. The processing chip 33 and the battery are embedded inside the heel portion 412. The first magnetic sensor 441 is connected to the processing chip 33 through a connecting line 442. A portion of the connecting line 442 is fixed on the heel portion 412 of the upper 410, and another portion is fixed on the heel portion 412 of the sole 420. The processing chip 33 and the battery are fixed at the heel portion 412 of the sole 420. An electrical signal output from a magnetic sensor (not shown) is transmitted to the processing chip 33 through the connecting line 442, and the processing chip 33 analyzes, calculates and records the received electrical signal. The battery supplies power to the magnetic sensor (not shown) and the processing chip 33 through the connecting line 442. The entire sensing device 300 adopts a miniaturized design, and each component is very small in size and light in weight, and does not excessively increase the weight of the sports shoe 400. Moreover, the entire sensing device 300 is at micro-ampere-level ultra-low power consumption, which can satisfy long-term continuous use.

Take football sports as an example, since the first magnetic sensor 441, the second magnetic sensor 444, the third magnetic sensor (not shown), the fourth magnetic sensor (not shown), and the fifth magnetic sensor (not shown) are fixed on a plurality of parts of the upper 410 of the sports shoe 400, when a wearer touches the football with the foot, the football (the football is internally provided with magnetic strips or magnetic sheets, so that the football has a magnetic field) approves a magnetic force to the second magnetic sensor 444, the third magnetic sensor (not shown), the fourth magnetic sensor (not shown), and the fifth magnetic sensor (not shown) at the touch parts of the upper 410. The magnetic sensors convert the subjected magnetic force into an electrical signal to be transmitted to the processing chip 33 through the connecting line 442, and the processing chip 33 can acquire ball touch parts according to the electrical signal of the magnetic sensors on the touch parts of the upper 410, and calculate and record ball touch times (the left and right feet) of the wearer according to the receiving times of the electrical signal. It should be particularly noted that the sports shoe 400 helps the football player or football fan to practice arc shot in the daily football training (the arc shot is also called "curve ball", "banana ball", which is a technical term in football sports. The arc shot refers to a kicking technique in which the player uses a foot method to kick the ball and make the ball run in the air in an arc. The arc shot is often used when the attacker gets a direct free kick near the opponent's penalty area, using an arc running state to avoid a wall and directly shoot for scoring). The sports shoe 400 helps the kicker find the best part of implementing the arc shot with the foot by sensing and recording the ball touch parts when the kicker practices the arc shot. A football player or football fan can quickly and better master this kicking technique with the help of the sports shoe 400.

The processing chip 33 can calculate whether the wearer dribbles or passes the ball according to the frequency of the electrical signal of the second magnetic sensor 444, the third magnetic sensor (not shown), the fourth magnetic sensor (not shown), and the fifth magnetic sensor (not shown) received from different positions on the upper 410, and the wearer's pass times and dribbling distances are calculated and recorded according to the electrical signal of the first magnetic sensor 441 on the heel portion 412. Finally, the processing chip 33 calculates the calorie consumption of the wearer throughout the whole exercise with reference to the calorie consumption of each exercise state according to the recorded running distance, running speed, pass times, dribbling distance, and the like.

To enable the reader to better understand the identification process of the player's ball touch action mentioned in the present application, examples are given below for description.

For the motion identification of kicking (dribbling) the ball, first, when the magnetic football is close to the football shoe worn by the player, the magnetic sensors sense changes of a magnetic field and emit a ball touch signal, and the processing chip identifies which magnetic sensor(s) give(s) the ball touch signal after receiving the ball touch signal, and determines ball touch parts of the left and right feet of the player and time points corresponding to the ball touch. Then, data of the acceleration sensor and the gyro sensor in several seconds before and after ball touch sensing time points in a memory of the processing chip is extracted to perform fusion analysis to accurately describe the trajectory of the whole action of kicking the ball, and then with reference to a postural mathematical model established in the cloud, whether the motion of kicking the ball is dribbling the ball, passing the ball, sliding tackle, smashing, dribbling, etc. can be identified, so as to display the technical analysis on an APP. Moreover, to improve the accuracy of motion identification, the Gauss Newton iterative algorithm is improved. The basic flow is: (ball touch sensing)→extracting data of the acceleration sensor in several seconds (adjustable) before and after the ball touch time points in the memory (filter processing has been completed after data sampling and before the storage)→obtaining an attitude error rate through Gauss-Newton iteration→measuring an attitude angle→extracting data of the gyro sensor at the same time→processing through a quaternion differential equation→calculating an attitude quaternion rate→performing fusion integration on acceleration and gyro data→attitude quaternion→Euler angle conversion→trajectory estimation-→(ball touch sensing)→mathematical model matching-→motion identification.

For example, for the "stepovers" dribbling motion identification: first, the magnetic sensors sense a ball touch signal, and the processing chip identified a situation that the left and right feet of a player streak across semicircles on the two sides of the ball (this action can be performed many times continuously), according to a forward arc of the player's two feet sensed by the gyro sensor disposed on the player's body and finally the magnetic sensors sense a secondary ball touch signal; in this way, the whole trajectory of the whole dribbling motion is described, and it can be identified that the dribbling motion is a "stepovers" motion with reference to the postural mathematical model established in the cloud.

Coaching staff can analyze technical problems of individual football players of the team and technical and tactical problems of the team as a whole according to the football players' kicking (dribbling) motions and the ball control rate, pass times and ball control time of both teams, and guide each football player and the team's football players to conduct more scientific and reasonable training.

The device embodiment described above are merely schematic, and units described as separate components may or may not be physically separated, and the components displayed as units may or may not be physical units, that is, the units and the components may be located in one place, or may be distributed to multiple network units. Some or all of modules may be selected according to actual needs to achieve the objective of the solution of the embodiment.

Through the description of the foregoing embodiments, those of ordinary skill in the art can clearly understand that the various embodiments can be implemented by means of software plus a general hardware platform, and certainly, by hardware. Those of ordinary skill in the art can understand that all or part of the process of implementing the foregoing embodiments can be completed by a computer program by instructing related hardware, and the program can be stored in a computer readable storage medium. When the program is executed, the flow of an embodiment of the methods as described above may be included. The storage medium may be a magnetic disk, an optical disk, a read-only memory (ROM), or a random access memory (RAM), etc.

Finally, it should be noted that the foregoing embodiments are only used to illustrate the technical solutions of the present application, and are not intended to limit the technical solutions; in the idea of the present application, the technical features in the foregoing embodiments or different embodiments may also be combined. The steps may be performed in any order, and there are many other variations of different aspects of the present application as described above, which are not provided in details for the sake of brevity. Although the present application has been described in detail with reference to the foregoing embodiments, those of ordinary skill in the art should understand that they can still modify the technical solutions recited in the foregoing embodiments, or perform equivalent substitutions on some of the technical features therein. Moreover, such modifications or substitutions do not make the essence of the corresponding technical solution depart from the scope of the technical solution of each embodiment of the present application.

What is claimed is:

1. A method for motion data processing, comprising:
   during training and match, receiving a touch ball data and a body motion data;
   the touch ball data comprising a ball touch part of the player, a ball touch times and a time point corresponding to the ball touch;
   the body motion data comprising a body moving direction and a body inclination angle of the player;
   wherein the step of receiving a touch ball data comprises:
   during training and match, a magnetic football provided with a plurality of magnetic sheets or magnetic strips;
   a football shoe worn by a football player provided with a plurality of magnetic sensors and processing chips;
   the magnetic sensor sensing the magnetic football and converting to electrical signal send to the processing chip;
   according to the electrical signal, analyzing a ball touch part of the player, a ball touch times and the time point corresponding to the ball touch by the processing chip;
   according to the touch ball data, generating a first statistical data;
   according to the touch ball data and the body motion data generating a second statistical data;
   according to the first statistical data, identifying the player's ball touch motion for dribbling and passing the football and analyzing the second statistical data in order to identifying the player's sliding tackle, smashing or dribbling;
   wherein the step of according to the first statistical data, identifying the player's ball touch motion for dribbling and passing the football and analyzing the second statistical data in order to identifying the player's sliding tackle, smashing or dribbling comprises;
   performing fusion analysis on the body moving direction and the body inclination angle of the player collected on a first predetermined time and a second predetermined time to describe a trajectory of the player's kicking motion; the first predetermined time is before the time point corresponding to the ball touch, the second predetermined time is after the time point corresponding to the ball touch;
   with reference to a postural mathematical model established in a cloud, identifying whether the player's kicking motion is sliding tackle, smashing or dribbling.

2. The method according to claim 1, wherein the step of receiving a body motion data comprises:
   sensing, by a six-axis sensor disposed on the player, the body moving direction and the body inclination angle of the player;
   recording time points corresponding to each body moving direction and a time point corresponding to each body inclination angle; and
   transmitting, by a first communication module disposed on the player, the body moving direction and the body inclination angle of the player to the processing chip in wireless transmission mode.

3. The method according to claim 2, wherein the method further comprises:
   receiving a third statistical data, the third statistical data comprising ball control rates, pass times and ball control time of both teams;
   wherein the step of receiving the third statistical data comprises:
   transmitting the first statistical data or the second statistical data acquired by the processing chip to a central processing unit outside the court by wirelessly connecting which is established by a fourth communication module disposed outside the court to a second communication module disposed on the football shoe;
   the central processing unit performing statistics and analysis on the received first statistical data and second statistical data of each player on the court;
   during training and match, providing the ball control rates, the pass times and the ball control time of both teams.

4. A system for motion data processing, comprising:
   a magnetic football provided with a plurality of magnetic sheets or magnetic strips;
   a sensing device configured to obtain a touch ball data, the touch ball data comprising ball touch parts of a player, ball touch times and time points corresponding to a ball touch;
   a sensing device comprised a processing chip and a plurality of magnetic sensors; the magnetic sensors respectively connected to the processing chip; the sensing device disposed on a football shoes and the magnetic sensors distributed on upper of the football shoes, configured to sense the ball touch parts, ball touch times and time points corresponding to the ball touch between the magnetic ball and the player and convert into electrical signal to be transmitted to the processing chip;

a six-axis sensor configured to receive a body motion data, the body motion data comprising a body moving direction of the player and a body inclination angle of the player;

a six-axis sensor comprised an acceleration sensor configured to sense a body moving direction of the player and record corresponding time point, and a gyro sensor configured to sense a body inclination angle of the player and record corresponding time point;

the body motion data transmitted by a first communication module disposed on the player to the processing chip in wireless transmission mode;

the processing chip configured to statistics and analysis to generate a first statistical data according to the touch ball data and generate a second statistical data according to the body motion data;

the processing chip configured to identifying the player's ball touch motion for dribbling and passing the football by analyzing the first statistical data and identifying the player's sliding tackle, smashing or dribbling by analyzing the second statistical data;

wherein the step of identifying the player's sliding tackle, smashing or dribbling by analyzing the second statistical data comprises:

performing fusion analysis on the body moving direction and the body inclination angle of the player collected on a first predetermined time and a second predetermined time to describe a trajectory of the player's kicking motion; the first predetermined time is before the time point corresponding to the ball touch, the second predetermined time is after the time point corresponding to the ball touch;

with reference to a postural mathematical model established in a cloud, identify whether the player's kicking motion is sliding tackle, smashing or dribbling.

5. The system according to claim 4, wherein the processing chip comprises at least three address lines.

6. The system according to claim 4, wherein the processing chip comprises threshold register.

\* \* \* \* \*